United States Patent
Breitkopf (12)

(10) Patent No.: US 6,756,521 B1
(45) Date of Patent: Jun. 29, 2004

(54) MOISTURE SENSING AND INDICATING SYSTEM

(76) Inventor: Norbert Breitkopf, 3255 Celestial Cir., Corona, CA (US) 92882

(*) Notice: Subject to any disclaimer, the term of this patent is extended or adjusted under 35 U.S.C. 154(b) by 526 days.

(21) Appl. No.: 09/765,596

(22) Filed: Jan. 22, 2001

(51) Int. Cl.$^7$ .................................................. A61F 13/15
(52) U.S. Cl. ...................... 604/361; 340/604; 340/605; 604/385.01
(58) Field of Search ............................ 604/361, 385.01; 340/604, 605, 573.5; 200/61.04

(56) References Cited

U.S. PATENT DOCUMENTS

| | | |
|---|---|---|
| 4,484,573 A | 11/1984 | Yoo |
| 5,036,859 A | 8/1991 | Brown |
| D326,423 S | 5/1992 | Clyde |
| 5,808,554 A | 9/1998 | Shuminov |
| 5,838,240 A * | 11/1998 | Johnson ...................... 340/604 |
| 5,868,723 A | 2/1999 | Al-Sabah |
| 5,908,411 A | 6/1999 | Matsunari |
| 6,097,297 A * | 8/2000 | Fard ........................... 340/604 |
| 6,200,250 B1 * | 3/2001 | Janszen ....................... 493/383 |

* cited by examiner

Primary Examiner—John J. Calvert
Assistant Examiner—Jacqueline F Stephens

(57) ABSTRACT

A moisture sensing and indicating system for signaling to a caretaker that a diaper has moisture therein. The moisture sensing and indicating system includes a casing having a plurality of apertures therein for accessing an interior of the casing. The casing is positioned between absorbent material and watertight material of a diaper. A sensor for detecting moisture is positioned in the casing. Moisture actuates the sensor by completing a circuit. A transmitter for transmitting a signal is positioned in the casing and operationally coupled to the sensor. A housing has a top wall, a bottom wall and a peripheral wall extending between integrally coupled to the top and bottom walls. The top wall has a plurality of openings therein. A receiver for receiving a signal from the transmitter is positioned in the housing. A speaker for emitting a sound is securely positioned in the housing and traverses the openings in the top wall. The speaker is operationally coupled to the receiver. The receiver sends a signal to the speaker such that the speaker emits a sound when the receiver receives a signal from the transmitter.

4 Claims, 5 Drawing Sheets

MOISTURE SENSING AND INDICATING SYSTEM

BACKGROUND OF THE INVENTION

1. Field of the Invention

The present invention relates to moisture sensing devices for diapers and more particularly pertains to a new moisture sensing and indicating system for signaling to a caretaker that a diaper has moisture therein.

2. Description of the Prior Art

The use of moisture sensing devices for diapers is known in the prior art. More specifically, moisture sensing devices for diapers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,036,859; 4,484,573; U.S. Des. Pat. No. 326,423; U.S. Pat. Nos. 5,868,723; 5,908,411; and 5,808,554.

While these devices fulfill their respective, particular objectives and requirements, the aforementioned patents do not disclose a new moisture sensing and indicating system. The inventive device includes a casing having a plurality of apertures therein for accessing an interior of the casing. The casing is positioned between absorbent material and watertight material of a diaper. A sensor for detecting moisture is positioned in the casing. Moisture actuates the sensor by completing a circuit. A transmitter for transmitting a signal is positioned in the casing and operationally coupled to the sensor. A housing has a top wall, a bottom wall and a peripheral wall extending between integrally coupled to the top and bottom walls. The top wall has a plurality of openings therein. A receiver for receiving a signal from the transmitter is positioned in the housing. A speaker for emitting a sound is securely positioned in the housing and traverses the openings in the top wall. The speaker is operationally coupled to the receiver. The receiver sends a signal to the speaker such that the speaker emits a sound when the receiver receives a signal from the transmitter.

In these respects, the moisture sensing and indicating system according to the present invention substantially departs from the conventional concepts and designs of the prior art, and in so doing provides an apparatus primarily developed for the purpose of signaling to a caretaker that a diaper has moisture therein.

SUMMARY OF THE INVENTION

In view of the foregoing disadvantages inherent in the known types of moisture sensing devices for diapers now present in the prior art, the present invention provides a new moisture sensing and indicating system construction wherein the same can be utilized for signaling to a caretaker that a diaper has moisture therein.

The general purpose of the present invention, which will be described subsequently in greater detail, is to provide a new moisture sensing and indicating system apparatus and method which has many of the advantages of the moisture sensing devices for diapers mentioned heretofore and many novel features that result in a new moisture sensing and indicating system which is not anticipated, rendered obvious, suggested, or even implied by any of the prior art moisture sensing devices for diapers, either alone or in any combination thereof.

To attain this, the present invention generally comprises a casing having a plurality of apertures therein for accessing an interior of the casing. The casing is positioned between absorbent material and watertight material of a diaper. A sensor for detecting moisture is positioned in the casing. Moisture actuates the sensor by completing a circuit. A transmitter for transmitting a signal is positioned in the casing and operationally coupled to the sensor. A housing has a top wall, a bottom wall and a peripheral wall extending between integrally coupled to the top and bottom walls. The top wall has a plurality of openings therein. A receiver for receiving a signal from the transmitter is positioned in the housing. A speaker for emitting a sound is securely positioned in the housing and traverses the openings in the top wall. The speaker is operationally coupled to the receiver. The receiver sends a signal to the speaker such that the speaker emits a sound when the receiver receives a signal from the transmitter.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new moisture sensing and indicating system apparatus and method which has many of the advantages of the moisture sensing devices for diapers mentioned heretofore and many novel features that result in a new moisture sensing and indicating system which is not anticipated, rendered obvious, suggested, or even implied by any of the prior art moisture sensing devices for diapers, either alone or in any combination thereof.

It is another object of the present invention to provide a new moisture sensing and indicating system which may be easily and efficiently manufactured and marketed.

It is a further object of the present invention to provide a new moisture sensing and indicating system which is of a durable and reliable construction.

An even further object of the present invention is to provide a new moisture sensing and indicating system which is susceptible of a low cost of manufacture with regard to both materials and labor, and which accordingly is then susceptible of low prices of sale to the consuming public, thereby making such moisture sensing and indicating system economically available to the buying public.

Still yet another object of the present invention is to provide a new moisture sensing and indicating system which provides in the apparatuses and methods of the prior art some of the advantages thereof, while simultaneously overcoming some of the disadvantages normally associated therewith.

Still another object of the present invention is to provide a new moisture sensing and indicating system for signaling to a caretaker that a diaper has moisture therein.

Yet another object of the present invention is to provide a new moisture sensing and indicating system which includes a casing having a plurality of apertures therein for accessing an interior of the casing. The casing is positioned between absorbent material and watertight material of a diaper. A sensor for detecting moisture is positioned in the casing. Moisture actuates the sensor by completing a circuit. A transmitter for transmitting a signal is positioned in the casing and operationally coupled to the sensor. A housing has a top wall, a bottom wall and a peripheral wall extending between integrally coupled to the top and bottom walls. The top wall has a plurality of openings therein. A receiver for receiving a signal from the transmitter is positioned in the housing. A speaker for emitting a sound is securely positioned in the housing and traverses the openings in the top wall. The speaker is operationally coupled to the receiver. The receiver sends a signal to the speaker such that the speaker emits a sound when the receiver receives a signal from the transmitter.

Still yet another object of the present invention is to provide a new moisture sensing and indicating system that has a housing having an annular member thereon for coupling the housing to a chain or other elongated flexible member for easy carrying of the housing.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
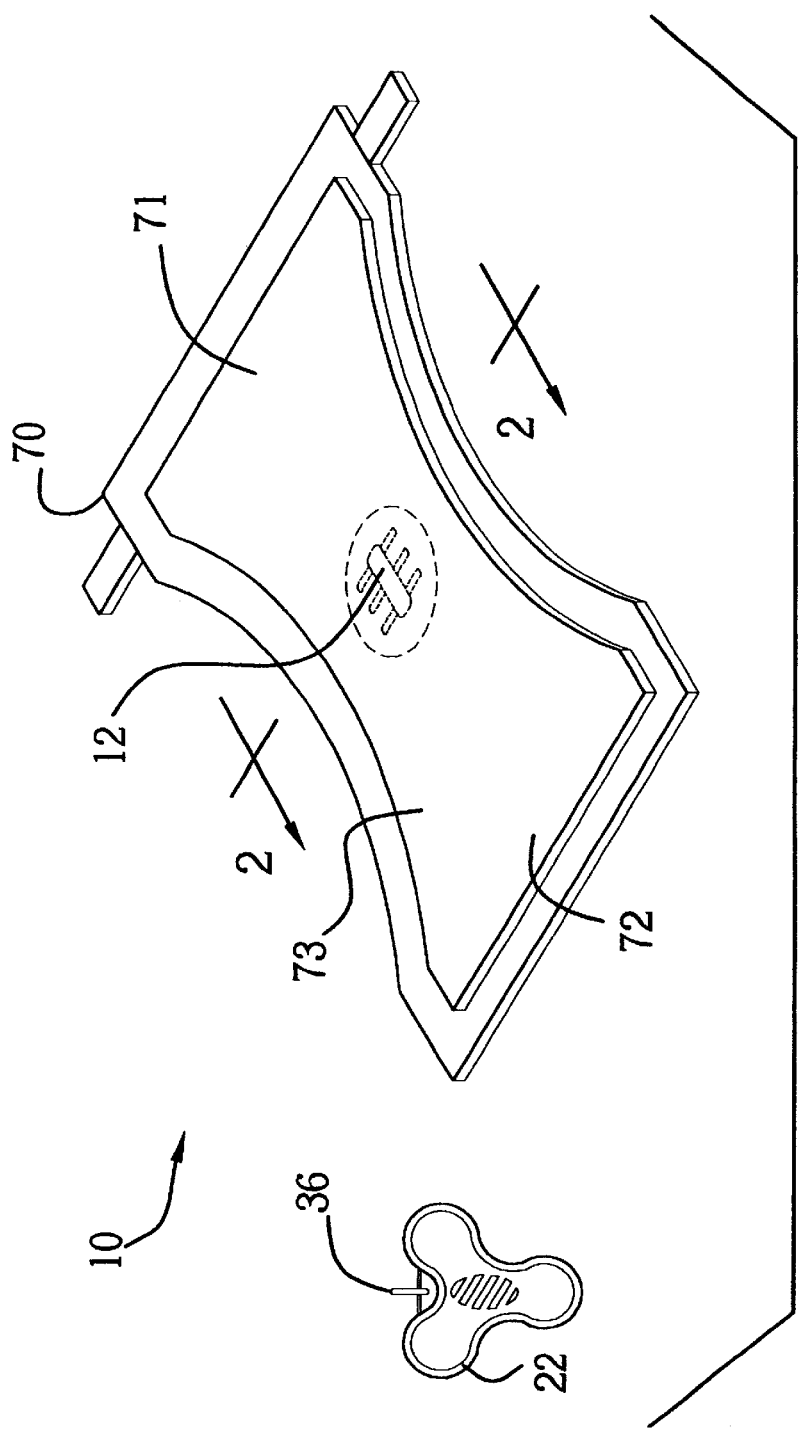
FIG. 1 is a schematic perspective view of a new moisture sensing and indicating system according to the present invention.
Figure 2:
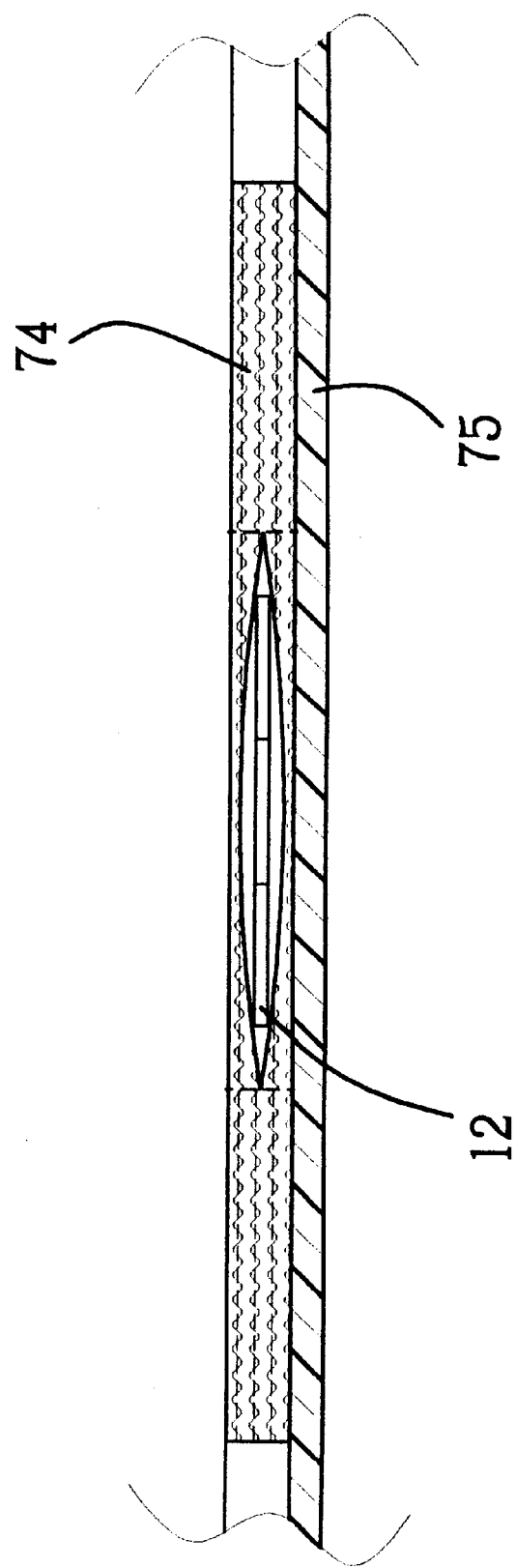
FIG. 2 is a schematic cross-sectional view taken along line 2—2 of the present invention.
Figure 3:
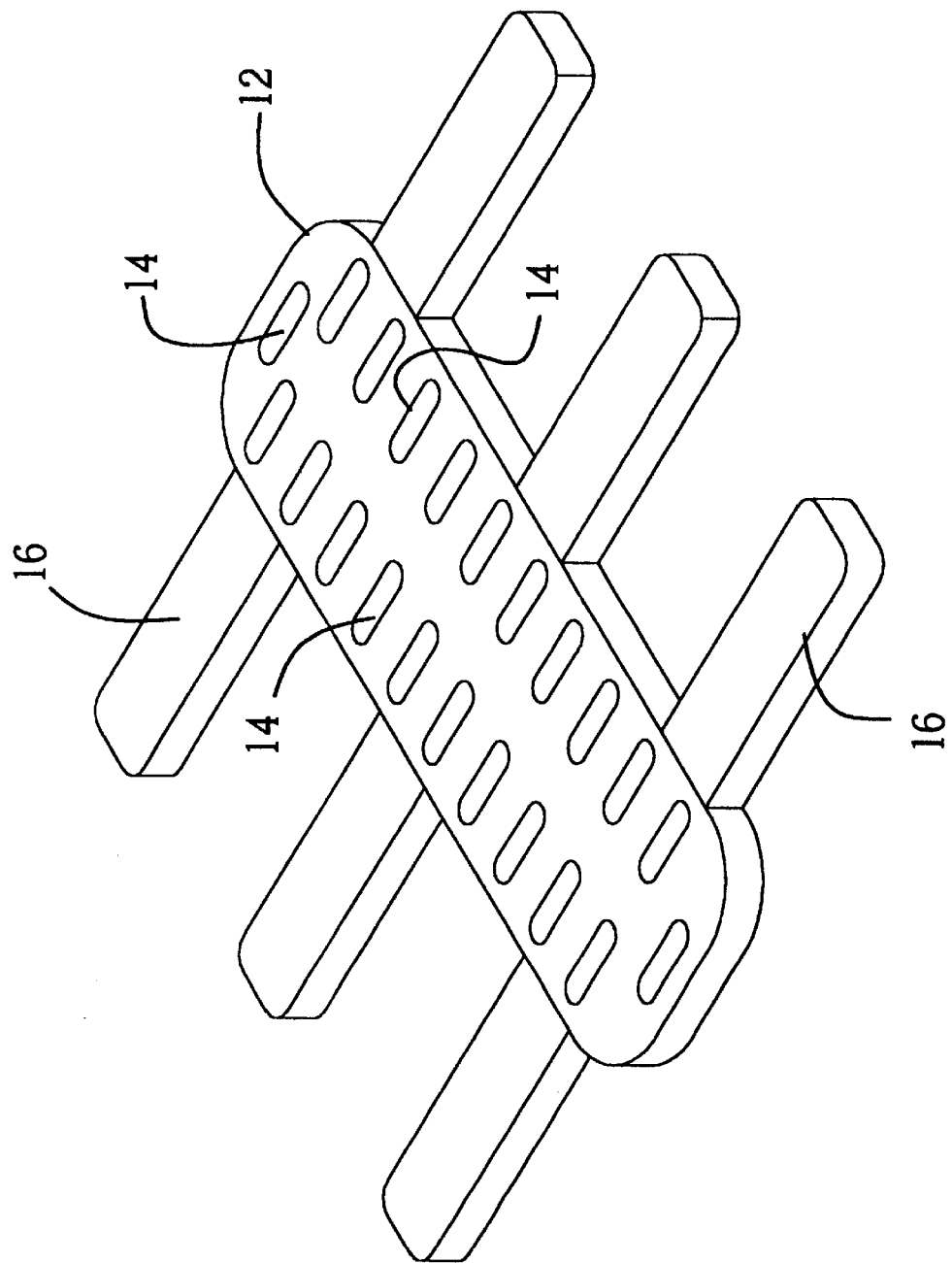
FIG. 3 is a schematic perspective view of the casing of the present invention.
Figure 4:
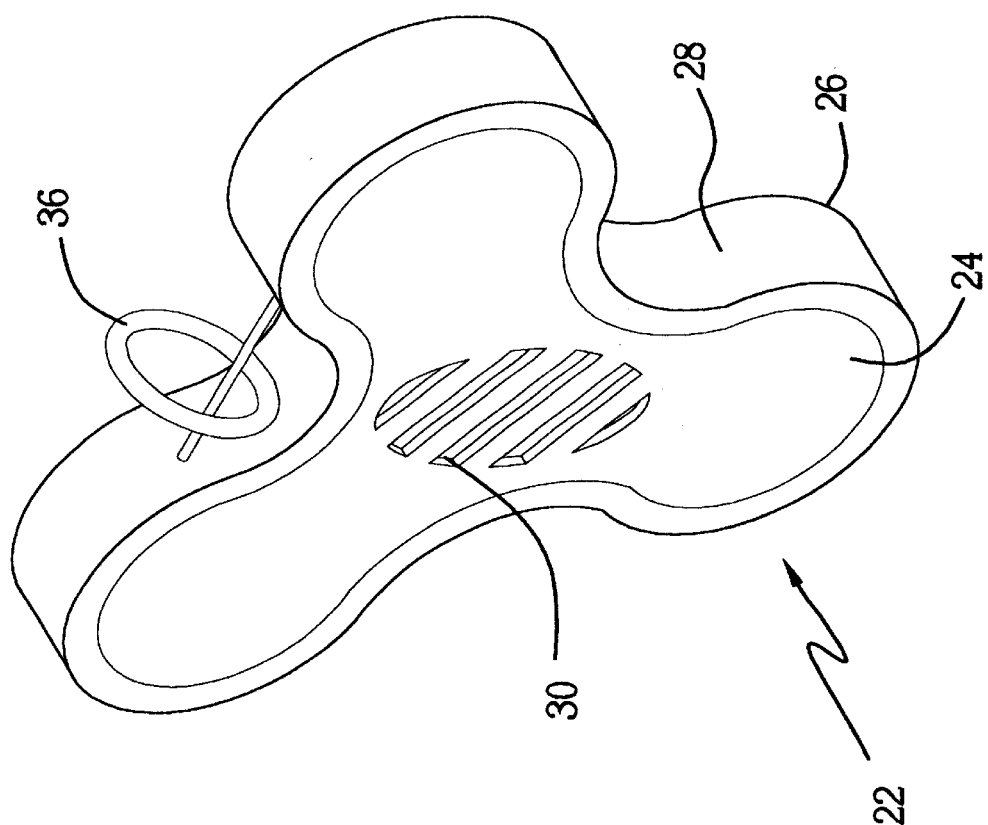
FIG. 4 is a schematic perspective view of the housing of the present invention.
Figure 5:
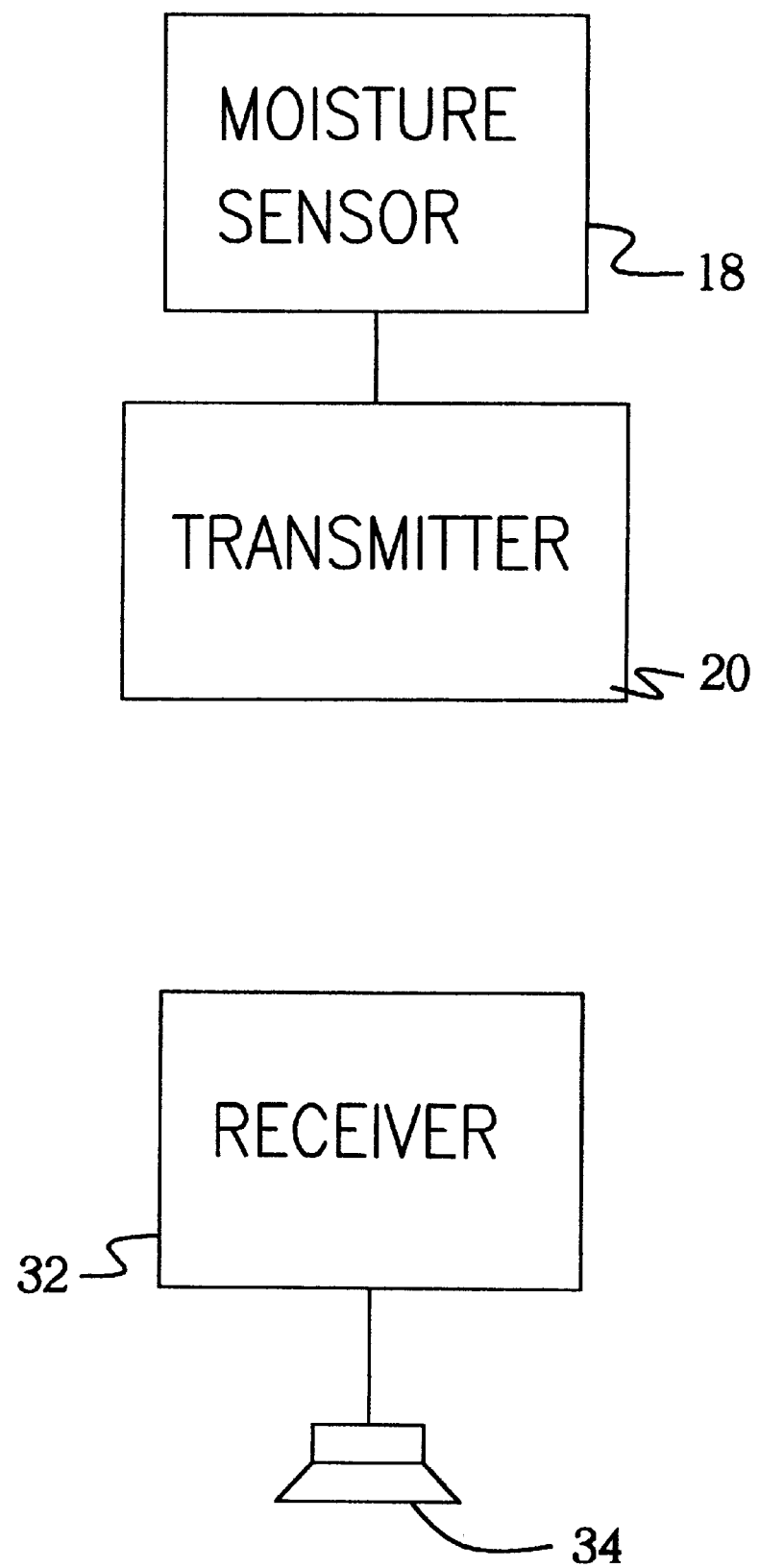
FIG. 5 is an electronic schematic view of the present invention.

With reference now to the drawings, and in particular to FIGS. 1 through 5 thereof, a new moisture sensing and indicating system embodying the principles and concepts of the present invention and generally designated by the reference numeral 10 will be described.

As best illustrated in FIGS. 1 through 5, the moisture sensing and indicating system 10 generally comprises a system for indicating the presence of moisture in a diaper 70. The diaper 70 has a rear portion 71, a front portion 72 and a central portion 73. The central portion 73 has a top layer 74 of absorbent material and a bottom layer 75 of generally watertight material and generally comprises a conventional disposable diaper.

A casing 12 has a plurality of apertures 14 therein for accessing an interior of the casing 12. The casing 12 is positioned between the absorbent material 74 and the watertight material 75 of the central portion 73 of the diaper 70.

A plurality of absorbent tabs 16 extends outwardly of the casing 12. Each of the tabs 16 is adapted for drawing moisture into the casing 12. A sensor 18 for detecting moisture is positioned in the casing 12. Moisture actuates the sensor 12 by completing a circuit once it enters the casing either through the apertures 14 or along the absorbent tabs 16. A transmitter 20 for transmitting a signal is positioned in the casing 12 and is operationally coupled to the sensor 18.

A housing 22 has a top wall 24, a bottom wall 26 and a peripheral wall 28 extending between and is operationally coupled to the top 24 and bottom 26 walls. The top wall 24 has a plurality of openings 30 therein. A receiver 32 for receiving a signal from the transmitter 20 is positioned in the housing 22. A speaker 34 for emitting a sound is securely positioned in the housing 22 and traverses the openings 30 in the top wall 24. The speaker 34 is operationally coupled to the receiver 32. An annular member 36 is rotatably coupled to the peripheral wall of the housing 22.

Preferably, a plurality of diapers 70 is provided each with a casing 12 and its respective components therein. Each of the transmitters 20 sends a signal to the receiver 32. The user needs only buy one receiver to work with all of the transmitters to keep the cost low and maintain an efficient use of resources.

In use, the receiver sends 32 a signal to the speaker 34 such that the speaker 34 emits a sound when the receiver 32 receives a signal from the transmitter 20. The audible sound signals a parent or guardian that the diaper 70 of the child is wet and requires changing. The annular member 36 allows the caretaker to place the housing 22 on chain, such as a necklace or bracelet for easy monitoring and carrying of the housing.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A moisture detector and indicator system for indicating the presence of moisture in a diaper, the diaper having a rear portion, a front portion and a central portion, said central portion having a top layer of absorbent material and a bottom layer of generally watertight material, said system comprising:

a casing, said casing having a plurality of apertures therein for accessing an interior of said casing, said casing being positioned between said absorbent material and said watertight material;

a sensor for detecting moisture, said sensor being positioned in said casing, wherein moisture actuates said sensor by completing a circuit;

a transmitter for transmitting a signal, said transmitter being positioned in said casing and operationally coupled to said sensor;

a housing having a top wall, a bottom wall and a peripheral wall extending between and being integrally coupled to said top and bottom walls, said top wall having a plurality of openings therein;

a receiver for receiving a signal from said transmitter, said receiver being positioned in said housing;

a speaker for emitting a sound being securely positioned in said housing and traversing said openings in said top wall, said speaker being operationally coupled to said receiver, wherein said receiver sends a signal to said speaker such that said speaker emits a sound when said receiver receives a signal from said transmitter; and a plurality absorbent tabs extending outwardly of said casing, each of said tabs being adapted for drawing moisture into said casing.

2. The moisture detector and indicator system as in claim 1, further including:

an annular member, said annular member being rotatably coupled to said peripheral wall of said housing.

3. A moisture detector and indicator system for indicating the presence of moisture in a plurality of diapers, the diapers each having a rear portion, a front portion and a central portion, each of the central portions having a top layer of absorbent material and a bottom layer of generally watertight material, said system comprising:

a plurality of casings, each of said casings having a plurality of apertures therein for accessing an interior of said casing, each of said casing being positioned in one of said central portions of said diapers and located between said absorbent material and said watertight material;

a plurality absorbent tabs extending outwardly of each of said casings, each of said tabs being adapted for drawing moisture into a respective one of said casings;

a plurality of sensors for detecting moisture, each of said sensors being positioned in one of said casing, wherein moisture actuates said sensors by completing a circuit;

a plurality of transmitters for transmitting a signal, each of said transmitters being positioned in one of said casing and operationally coupled to a respective one of said sensors;

a housing having a top wall, a bottom wall and a peripheral wall extending between and being integrally coupled to said top and bottom walls, said top wall having a plurality of openings therein;

a receiver for receiving a signal from said transmitters, said receiver being positioned in said housing;

a speaker for emitting a sound being securely positioned in said housing and traversing said openings in said top wall, said speaker being operationally coupled to said receiver, wherein said receiver sends a signal to said speaker such that said speaker emits a sound when said receiver receives a signal from one of said transmitters; and an annular member, said annular member being rotatably coupled to said peripheral wall of said housing.

4. A moisture detector and indicator system for indicating the presence of moisture in a diaper, the diaper having a rear portion, a front portion and a central portion, said central portion having a top layer of absorbent material and a bottom layer of generally watertight material, said system comprising:

a casing, said casing having a plurality of apertures therein for accessing an interior of said casing, said casing being positioned between said absorbent material and said watertight material;

a sensor for detecting moisture, said sensor being positioned in said casing, wherein moisture actuates said sensor by completing a circuit;

a transmitter for transmitting a signal, said transmitter being positioned in said casing and operationally coupled to said sensor;

a housing having a top wall, a bottom wall and a peripheral wall extending between and being integrally coupled to said top and bottom walls, said top wall having a plurality of openings therein;

a receiver for receiving a signal from said transmitter, said receiver being positioned in said housing;

a speaker for emitting a sound being securely positioned in said housing and traversing said openings in said top wall, said speaker being operationally coupled to said receiver, wherein said receiver sends a signal to said speaker such that said speaker emits a sound when said receiver receives a signal from said transmitter; and an annular member, said annular member being rotatably coupled to said peripheral wall of said housing.

* * * * *